(12) United States Patent
Hacini-Rachinel et al.

(10) Patent No.: US 11,234,959 B2
(45) Date of Patent: Feb. 1, 2022

(54) COMPOSITIONS COMPRISING A COMPOUND OF THE AVERMECTIN FAMILY FOR THE TREATMENT AND/OR PREVENTION OF HAND ECZEMA

(71) Applicant: GALDERMA HOLDING SA, La Tour-De-Peilz (CH)

(72) Inventors: Feriel Hacini-Rachinel, Biot (FR); André Jomard, Saint Vallier de Thiey (FR); Jean Jacovella, Antibes (FR); Emmanuel Vial, Nice (FR)

(73) Assignee: GALDERMA HOLDING SA, La Tour-de-Peilz (CH)

( * ) Notice: Subject to any disclaimer, the term of this patent is extended or adjusted under 35 U.S.C. 154(b) by 0 days.

(21) Appl. No.: 16/347,155

(22) PCT Filed: Nov. 2, 2017

(86) PCT No.: PCT/EP2017/078095
§ 371 (c)(1),
(2) Date: May 2, 2019

(87) PCT Pub. No.: WO2018/083196
PCT Pub. Date: May 11, 2018

(65) Prior Publication Data
US 2020/0054599 A1 Feb. 20, 2020

(30) Foreign Application Priority Data

Nov. 3, 2016 (EP) .................................... 16306438

(51) Int. Cl.
*A61K 31/365* (2006.01)
*A61P 17/00* (2006.01)
*A61K 47/02* (2006.01)
*A61K 9/00* (2006.01)
*A61K 9/06* (2006.01)
*A61K 47/10* (2017.01)
*A61K 47/14* (2017.01)
*A61K 47/18* (2017.01)

(52) U.S. Cl.
CPC .......... *A61K 31/365* (2013.01); *A61K 9/0014* (2013.01); *A61K 9/06* (2013.01); *A61K 47/02* (2013.01); *A61K 47/10* (2013.01); *A61K 47/14* (2013.01); *A61K 47/183* (2013.01); *A61P 17/00* (2018.01)

(58) Field of Classification Search
CPC .................................................. A61K 31/365
See application file for complete search history.

(56) References Cited

U.S. PATENT DOCUMENTS

2012/0034226 A1* 2/2012 Yoshida ................. A61K 45/06
424/135.1

FOREIGN PATENT DOCUMENTS

WO  WO 2015/079016 A1  6/2015

OTHER PUBLICATIONS

International Search Report issued in PCT/EP2017/078095, dated Dec. 22, 2017.
Written Opinion of the International Searching Authority issued in PCT/EP2017/078095, dated Dec. 22, 2017.
Diepgen et al., "Management of chronic hand eczema", Contact Dermatitis, vol. 57, (2007), pp. 203-210 (8 pages).
Hauber et al., "Benefit-risk tradeoff preferences for chronic hand eczema treatments", Journal of Dermatological Treatment, vol. 28, No. 1, (2017), pp. 40-46 (8 pages).

* cited by examiner

*Primary Examiner* — Yong S. Chong
(74) *Attorney, Agent, or Firm* — Foley & Lardner LLP; Sunit Talapatra

(57) ABSTRACT

The present invention relates to a pharmaceutical composition comprising a compound of the avermectin family, preferably ivermectin, in a pharmaceutically acceptable carrier, for use in the treatment and/or prevention of hand eczema.

9 Claims, No Drawings

COMPOSITIONS COMPRISING A COMPOUND OF THE AVERMECTIN FAMILY FOR THE TREATMENT AND/OR PREVENTION OF HAND ECZEMA

CROSS-REFERENCE TO RELATED APPLICATIONS

This application is the National Phase of International Patent Application No. PCT/EP2017/078095, filed Nov. 2, 2017, and published on Nov. 5, 2018 as WO WO/2018/083196 A1, which claims priority to European Patent Application No. 16306438.9, filed Nov. 3, 2016. The contents of these applications are herein incorporated by reference in their entirety.

The present invention relates to pharmaceutical compositions which are suitable for the treatment and/or prevention of hand eczema.

BACKGROUND OF THE INVENTION

Hand eczema (also known as hand dermatitis) is a common condition affecting up to 10% of the population. It is estimated that 5-7% of them have a chronic severe hand eczema, being defined by an hand eczema that persists more than 3 months or recurs at least 2 time in a year despite the use of standard therapies (Diepgen et al.: Contact Dermatitis 2007, 57, 203-210; and Hauber et al.: Journal of dermatological treatment, 2016, 28(1), 40-46). Conventional treatments include for instance topical treatments using bland emollients, corticosteroid creams or ointments, coal tar and derivatives, and calcineurin inhibitors; and systemic treatments such as azathioprine, cyclosporine, and retinoids, which are generally associated with significant side effects such as teratogenicity, psychiatric effects and lipids abnormalities.

Hand eczema usually results from a combination of factors, both internal (atopy: endogenous factors), and external (e.g. contact with irritants and allergens such as chemicals). The irritant nature of some chemicals means that hand eczema is particularly common in people with jobs involving cleaning, catering, hairdressing, healthcare and mechanical work. Occupation-related hand eczema is one of the most frequent occupational disease in many countries. It is an inflammatory condition, not contagious. Furthermore, occupational, domestic, social and psychological impacts of hand eczema are highly significant, especially for chronic hand eczema.

The main symptoms of hand eczema include one or more of the following:
Redness (erythema),
Itchings,
Pain,
Dryness, to the point of peeling and flaking,
Cracks (fissures), and
Blisters (vesicles).

Hand eczema is an increasingly common inflammatory skin disorder due to complex interactions between the genetic predispositions and environmental factors. It has a complex etiology that involves abnormal immunological and inflammatory pathways that include defective skin barrier, exposure to environmental agents and neuropsychological factors. The diagnosis is currently based on clinical presentation of skin erythematous plaques, eruption, and/or lichenification on the hands, accompanied by intense pruritus and cutaneous hypersensitivity.

Several clinical subtypes particularly include:
Pompholyx,
Fissured hand eczema also named housewives dermatitis,
Hyperkeratotic hand eczema,
Nummular eczema, and
Fingertips eczema or pulpitis.

Pompholyx is often used interchangeably with dyshidrotic eczema. This reflects the finding that perspiration volume was found to be greater in patients with pompholyx. Pompholyx is the symmetric development of vesicles on the lateral aspect of the fingers preceded by pruritis. Vesicles typically last approximately 2 to 4 weeks before resolving, and then recur at varying intervals.

Fissured hand eczema is dry eczema with scaling and fissuring and few hyperkeratotic areas. Exudation does not occur, and pruritus is minimal. It is seen in longstanding hand eczema, persisting for months to years.

Hyperkeratotic hand eczema is a chronic disease that consists of symmetric dense and adherent scaling on the palmar surface. It is most common in middle aged men. The cause is not usually identifiable but may be a result of allergy or chronic irritation. The clinical course is usually chronic and stable, and treatment should resemble that used for other forms of chronic hand eczema.

Nummular hand dermatitis is an unknown cause and presents with circular areas of redness, scaling, and erythema that are usually seen on the backs of the hands. Symptoms may also be present on the extremities. The inflammation is often subacute or chronic and may appear psoriatic. Once present, the size of the lesions does not usually change.

Fingertips eczema is hyperkeratotic eczema with painful fissures, which may extend to merge with eczema over the palm. Vesicles may occur. When all fingers, especially those of the dominant hand are involved, with aggravation in cold climate, this is possibly a cumulative irritant dermatitis where degreasing agents and trauma play a role.

For all these various types of hand eczema the most effective treatment is to avoid all contact with the causative agent. However this solution is not always feasible. Most of the time the administration of topical pharmaceutical compositions is needed such as emollient compositions, natural or synthetic immune inhibitors, anti-histaminic agents and steroids can also be used in pharmaceutical compositions for treating hand eczema. However, these compositions can be used only for a limited period of time, especially topical steroids. Indeed after a certain period of treatment especially with steroids, the skin becomes thinner. Regarding the topical immunomodulators there are relatively new treatments and the most common prescribed immunomodulator in this indication, Tacrolimus, marked under the name Prograf®, Advagraf® and Protopic®, is suspected of carrying cancer risk.

According to the complexity of the various hand eczema pathophysiologies and the side effects of the current treatments, there is a need for developing new pharmaceutical compositions useful for treating and/or preventing hand eczema, particularly chronic hand eczema.

SUMMARY OF THE INVENTION

In this context, the inventors have surprisingly provided a pharmaceutical composition comprising a compound of the avermectin family such as ivermectin, which can be effectively used for treating and/or preventing hand eczema, especially chronic hand eczema with no side effect.

The present invention herein provides a pharmaceutical composition comprising a compound of the avermectin family in a pharmaceutically acceptable carrier, for use in the treatment and/or prevention of hand eczema, preferably chronic hand eczema.

In a particular embodiment, the compound of the avermectin family is selected from the group consisting of ivermectin, avermectin, abamectin, doramectin, eprinomectin and selamectin, aversectin B, AB or C, emamectin B1a, emamectin B1b and their derivatives. More preferably, the compound of the avermectin family is ivermectin.

In a further particular embodiment, the composition as disclosed herein is to be administered by topical application on hands, preferably said composition is in the form of an emulsion, a cream, a lotion type, a gel or a solution.

In a preferred embodiment, the composition comprises from 0.001 to 5%, preferably from 0.01 to 2% and more preferably about 0.01, 0.03, 0.1, 0.3, 1 or 2% by weight of said compound of the avermectin family, relative to the total weight of the composition.

In a more preferred embodiment, the composition comprises:

| | |
|---|---|
| Ivermectin | 1.0 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| water | qs 100, | as % by weight relative to the total weight of the composition.

In a further more preferred embodiment, the composition comprises:

| | |
|---|---|
| Ivermectin | 0.3 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| water | qs 100, | as % by weight relative to the total weight of the composition.

DETAILED DESCRIPTION OF THE INVENTION

The inventors have surprisingly identified that a compound of the avermectin family, particularly ivermectin, presents a therapeutic interest for treating and/or preventing hand eczema.

Accordingly, the present invention relates to a pharmaceutical composition comprising a compound of the avermectin family in a pharmaceutically acceptable carrier, for use in the treatment and/or prevention of hand eczema.

Within the context of the present invention, the term "hand" includes all parts of the hands, such as the palm, the back, the fingers, and the fingertips.

The present invention also relates to a method for treating and/or preventing hand eczema, comprising administering an effective amount of a composition comprising a compound of the avermectin family in a pharmaceutically carrier, to a subject suffering of hand eczema. Particularly, the method is applied to a subject having hands with eczema, and/or hands for which hand eczema has been diagnosed, and/or hands susceptible to develop hand eczema.

The present invention also concerns the use of a pharmaceutical composition comprising a compound of the avermectin family in a pharmaceutically acceptable carrier for the preparation of a drug for treating and/or preventing hand eczema.

Particularly, the methods and the compositions as disclosed herein are directed to the treatment and/or prevention of chronic hand eczema.

Particularly, the compositions as disclosed herein are for use in the treatment of pompholyx, and/or fissured hand eczema, and/or hyperkeratotic, and/or hand eczema, and/or nummular eczema, and/or fingertips eczema.

In one embodiment, the term "treatment" or "treating" refers to an improvement or prophylaxis of hand eczema, or at least one symptom of hand eczema. In another embodiment, "treatment" or "treating" means an improvement or prevention of at least one measurable physical parameter associated with the disease or disorder being treated, which is not necessarily discernible in the subject. In another further embodiment, "treatment" or "treating" refers to inhibiting or slowing the progression of hand eczema, physically, e.g., stabilization of a discernible symptom, physiologically, for example, stabilization of a physical parameter, or both. In another embodiment, "treatment" or "treating" refers to delaying the onset of hand eczema or anyone of symptoms thereof. In some embodiments, compounds of interest are administered as a preventive measure. In this context, "prevention" or "preventing" refers to a reduction in the risk of acquiring a disease or disorder as specified herein.

As used herein, at least one of symptoms of hand eczema refers more specifically to redness, and/or itchings, and/or pain, and/or dryness, and/or cracks, and/or blisters, of hands or any part thereof.

As used herein, the term "pharmaceutical composition" refers preferably to a dermatological composition, which can be topically applied.

As used herein, "an effective amount" means the quantity sufficient for preventing and/or treating hand eczema and/or chronic hand eczema.

In a particular embodiment, the compound of the avermectin family is selected from the group consisting of ivermectin, avermectin, abamectin, doramectin, eprinomectin and selamectin, aversectin B, AB or C, emamectin B1a, emamectin B1b and their derivatives. More preferably, the compound of the avermectin family is ivermectin.

Ivermectin is a mixture of two compounds belonging to the avermectin class, 5-O-demethyl-22,23-dihydroavermectin A1a and 5-O-demethyl-22,23-dihydroavermectin A1b. They are also known as 22,23-dihydroavermectin B1a and 22,23-dihydroavermectin B1b. Ivermectin contains at least 80% of 22,23-dihydroavermectin B1a and less than 20% of 22,23-dihydroavermectin B1b. This active agent is part of the avermectin class, a group of macrocyclic lactones produced by the bacterium *Streptomyces avermitilis*.

In the middle of the 1980s, ivermectin was presented as a broad-spectrum antiparasitic medicinal product for veterinary use (Campbell et al.: Science, 1983, 5 221, 823-828). Ivermectin is effective against most common intestinal worms, except tapeworms, most acarids and some lice. In particular, it exhibits considerable affinity for the glutamate dependent chloride channels present in invertebrate nerve cells and muscle cells. Its binding to these channels promotes an increase in membrane permeability to chloride ions, resulting in hyperpolarization of the nerve or muscle cell. Neuromuscular paralysis which can lead to the death of certain parasites results therefrom. Ivermectin also interacts with other ligand dependant chloride channels, such as those involving the neuromediator GABA (gammaaminobutyric acid).

Ivermectin is more particularly disclosed as an anthelmintic used in humans for the treatment of river blindness caused by *Onchocerca volvulus*, of gastrointestinal strongyloidiasis (anguillulosis) (product Stromectol®), and of human scabies (Meinking et al., N. Engl. J. Med., 1995, 333, 26-30)) and also for the treatment of microfilaraemai diagnosed or suspected in individuals suffering from lymphatic filariasis due to *Wuchereria bancrofti*.

Manetta and Watkins (WO 2004/093886) have suggested the use of ivermectin for producing a topical pharmaceutical composition for the treatment of rosacea and other dermatologic conditions. However, ivermectin has never been disclosed or suggested in compositions for the treatment of hand eczema, especially by topical application on hands.

According to the invention, the pharmaceutical composition is formulated in a pharmaceutically acceptable carrier meaning that the pharmaceutical composition comprises a compound of the avermectin family in association with a pharmaceutically acceptable carrier.

The carrier must be "acceptable" in the sense of being compatible with the other ingredients of the formulations and not deleterious to the recipient thereof. Particularly, in the context of the invention, the carrier is compatible with human skin.

Suitable examples of carrier or base include, but not limited to, water, glycols, alcohols, lotions, creams, gels, emulsions, and sprays. Following examples provide various topical pharmaceutical compositions containing an avermectin compound for treatment of hand eczema and chronic hand eczema.

The pharmaceutical composition is advantageously administered by topical application and, therefore, is in a form suitable for topical application to the skin. For example, it may be in the form of an optionally gelled, oily solution, an optionally two-phase dispersion of the lotion type, an emulsion obtained by dispersion of a fatty phase in an aqueous phase (O/W) or vice versa (W/O), or a triple emulsion (W/O/W or O/W/O) or a vesicular dispersion of ionic and/or non-ionic type.

This topical composition may be in anhydrous form, in aqueous form or in the form of an emulsion. These compositions are prepared according to the usual methods.

According to this invention, a composition in the form of an emulsion obtained by dispersion of a fatty phase in an aqueous phase (O/W) is preferably used.

This composition may be more or less fluid and may be in the form of salves, emulsions, creams, milks, ointments, impregnated pads, syndets, solutions, gels, sprays or aerosols, foams, suspensions, lotions or sticks. Preferably, the composition used in the present invention is in the form of an emulsion, of a cream, of a lotion type, of a gel, or of a solution, and more preferably in the form of an emulsion.

The composition of the invention is preferably formulated according to the formulations disclosed in the patent application WO 2004/093886. Some formulations are illustrated by example 1.

The composition of the invention comprises from 0.001 to 5%, by weight of a compound of the avermectin family relative to the total weight of the composition. Preferably, the composition comprises from 0.01 to 2% by weight of a compound of the avermectin family relative to the total weight of the composition. Advantageously, the composition comprises about 0.01, 0.03, 0.1, 0.3, 1 or 2% by weight of a compound of the avermectin family relative to the total weight of the composition.

As used herein, the term "about" will be understood by a person of ordinary skill in the art and will vary to some extent on the context in which it is used. If there are uses of the term which are not clear to persons of ordinary skill in the art given the context in which it is used, "about" will mean up to plus or minus 20%, preferably 10% of the particular term.

In a specific embodiment, the pharmaceutical composition according to the present invention comprise one or more avermectin family compounds, one or more solvents for the active agent, an oily phase, one or more surfactants as emulsifier, and water.

In a preferred embodiment, the composition comprises in water:

| Ivermectin | 1.0 |
|---|---|
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH | as % by weight relative to the total weight of the composition.

A useful composition according to the present invention is Soolantra® launched by Galderma, which is a cream comprising 1% of ivermectin.

In a further more preferred embodiment, the composition comprises:

| Ingredients | % by weight relative to the total weight of the composition |
|---|---|
| Ivermectin | 0.3 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| water | qs 100, | as % by weight relative to the total weight of the composition.

According to another aspect, the present invention also relates to a method for treating and/or preventing hand eczema comprising administering to a subject suffering of hand eczema an effective amount of a composition comprising a compound of the avermectin family in a pharmaceutically carrier.

The present invention further relates to a method for treating and/or preventing symptoms of hand eczema, particularly redness, and/or itchings, and/or pain, and/or dryness, and/or cracks, and/or blisters, comprising administering to a subject in need thereof, an effective amount of a composition or a compound of the avermectin family as disclosed herein.

The present invention further relates to a method for treating pompholyx, and/or fissured hand eczema, and/or hyperkeratotic, and/or hand eczema and/or nummular eczema and/or fingertips eczema, comprising administering to a subject in need thereof, an effective amount of a composition or a compound of the avermectin family as disclosed herein.

For instance, the composition can be applied once daily to several times daily, once a week to several times a week. In a preferred embodiment the composition according to the present invention is administered once a day.

The present invention is directed to any mammal, particularly humans, male or female, infants, children, adults or elderly persons.

Following examples illustrate further aspect and advantages of the invention which are no way limiting in nature.

EXAMPLES

Example 1: Compositions of the Invention

Example 1a: Composition 1

| Ingredients | % by weight relative to the total weight of the composition |
|---|---|
| Ivermectin | 1.00 |
| Glycerol | 4.0 |
| Aluminium magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 2.5 |
| Steareth-20 | 3.0 |
| Sorbitan stearate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 1b: Composition 2

| Ingredients | % by weight relative to the total weight of the composition |
|---|---|
| Ivermectin | 1.00 |
| Glycerol | 4.0 |
| Steareth-2 | 1.0 |
| Steareth-21 | 2.0 |
| Aluminium magnesium silicate/titanium dioxide/silica | 1.0 |
| Methyl para-hydroxybenzoate | 0.2 |
| Propyl para-hydroxybenzoate | 0.1 |
| Disodium EDTA | 0.05 |
| Citric acid monohydrate | 0.05 |
| Isopropyl palmitate | 4.0 |
| Glyceryl/PEG 100 stearate | 2.0 |
| Self-emulsifiable wax | 1.0 |
| Palmitostearic acid | 2.00 |
| Dimethicone 20-350 cS | 0.5 |
| Propylene glycol | 4.0 |
| Glyceryl triacetate | 1.00 |
| Phenoxyethanol | 0.5 |
| 10% sodium hydroxide | qs pH |
| Water | qs 100 |

Example 1c: Composition 3

| Ingredients | % by weight relative to the total weight of the composition |
|---|---|
| Ivermectin | 1.00 |
| Glycerol | 4.0 |
| Acrylate C10-30 alkyl acrylate crosspolymer | 0.15 |
| Methyl para-hydroxybenzoate | 0.2 |
| Disodium EDTA | 0.05 |
| Citric acid monohydrate | 0.05 |
| Isopropyl myristate | 4.0 |
| Cetyl alcohol | 3.0 |
| Stearyl alcohol | 2.0 |
| Self-emulsifiable wax | 0.8 |
| Palmitostearic acid | 0.5 |
| Steareth-20 | 2.0 |
| Sorbitan palmitate | 1.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 1d: Composition 4

| Ingredients | % by weight relative to the total weight of the composition |
|---|---|
| Ivermectin | 1.00 |
| Glycerol | 4.0 |
| Aluminium magnesium silicate | 1.0 |
| Methyl para-hydroxybenzoate | 0.2 |
| Disodium EDTA | 0.05 |
| Citric acid monohydrate | 0.05 |
| Isopropyl palmitate | 4.0 |
| Glyceryl/PEG 100 stearate | 3.0 |
| Self-emulsifiable wax | 2.0 |
| Palmitostearic acid | 3.0 |
| Steareth-20 | 3.0 |
| Sorbitan palmitate | 2.0 |
| Dimethicone 20 | 0.5 |
| Propyl para-hydroxybenzoate | 0.1 |
| Propylene glycol | 4.0 |
| Glyceryl triacetate | 1.0 |
| Phenoxyethanol | 0.5 |
| 10% sodium hydroxide | qs pH |
| Water | qs 100 |

Example 1e: Composition 5

| Ingredients | % by weight relative to the total weight of the composition |
|---|---|
| Ivermectin | 1.00 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 1f: Composition 6

| Ingredients | % by weight relative to the total weight of the composition |
|---|---|
| Ivermectin | 1.4 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 1g: Composition 7

| Ingredients | % by weight relative to the total weight of the composition |
|---|---|
| Ivermectin | 0.3 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20cs | 0.5 |
| Propyl para-hydroxybenzoate | 0.1 |
| Propylene glycol | 2.0 |
| Phenoxyethanol | 1.0 |
| 10% sodium hydroxide | qs pH |
| Water | qs 100 |

Example 2: Clinical Trial

An ivermectin 0.3% cream (Composition 7 of the example 1g) has been applied once daily and compared to its vehicle (Composition 7 without ivermectin) in a 6-week clinical trial on 18 patients with moderate to severe hand eczema.

The severity of hand eczema was assessed using Investigator's Global Assessment (IGA) score (Duman and Uzunali, The European Research Journal, 2015, 1(2), 44-49). IGA consists of a 5-level scale:

0: Clear (No signs of hand eczema)

1: Almost clear (just perceptible scaling, and/or erythema);

2: Mild (mild scaling and/or mild erythema, and/or mild cracking);

3: Moderate (moderate scaling and/or erythema, and/or moderate cracking/fissuring);

4: Severe (severe scaling and/or severe erythema, and/or severe cracking/fissuring).

The results are presented in the tables 1 and 2 below:

TABLE 1

| Vehicle group | | | | | | | | | |
|---|---|---|---|---|---|---|---|---|---|
| | Subjects from vehicle group | | | | | | | | |
| | 1 | 2 | 3 | 4 | 5 | 6 | 7 | 8 | 9 |
| Severity at baseline (Mean of the 5 areas) | 3 | 3 | 3 | 3 | 3 | 3 | 4 | 3 | 3 |
| Severity after 6 weeks (Mean of the 5 areas) | 3 | 3 | 3 | 3 | 3 | 2 | 3 | 3 | 3 |

0: Clear
1: Almost clear
2: Mild
3: Moderate
4: Severe

TABLE 2

| ivermectin 0.3% group | | | | | | | | | |
|---|---|---|---|---|---|---|---|---|---|
| | Subjects from ivermectin 0.3% group | | | | | | | | |
| | 1 | 2 | 3 | 4 | 5 | 6 | 7 | 8 | 9 |
| Severity at baseline (Mean of the 5 areas) | 3 | 3 | 3 | 3 | 3 | 3 | 3 | 3 | 3 |
| Severity after 6 weeks (Mean of the 5 areas) | 3 | 3 | 1 | 3 | 3 | 2 | 1 | 2 | 3 |

0: Clear
1: Almost clear
2: Mild
3: Moderate
4: Severe

After 6 weeks of treatment, it has been observed that hand eczema is improved from moderate to almost clear or mild hand eczema (using a 5-point investigator global assessment (IGA)) for 44% (4/9) of the patients treated with ivermectin 0.3% whereas hand eczema is improved from moderate to mild hand eczema for only 11% (1/9) of the patients treating with the vehicle.

Therefore, the inventors have demonstrated that a composition comprising ivermectin, even at a low concentration of 0.3%, is useful for treating hand eczema.

The invention claimed is:

1. A method of treating and/or preventing hand eczema, comprising administering to a subject in need thereof an effective amount of a pharmaceutical composition comprising:
   0.3% to 2% by weight, relative to the total weight of the composition, of ivermectin; and
   a pharmaceutically acceptable carrier.

2. The method according to claim 1, wherein the hand eczema is chronic hand eczema.

3. The method according to claim 1, wherein the administering is topical application.

4. The method according to claim 1, wherein the composition is in the form of an emulsion, of a cream, of a lotion type, of a gel or of a solution.

5. The method according to claim 1, wherein the composition comprises from 1% to 2%, by weight, of ivermectin, relative to the total weight of the composition.

6. The method according to claim 1, wherein the composition comprises about 0.3, 1, or 2%, by weight, of ivermectin, relative to the total weight of the composition.

7. The method according to claim 1, wherein the composition comprises:
Ivermectin 1.0
Glycerol 4.0
Acrylate C10-30 alkyl acrylate crosspolymer 0.2
Methyl para-hydroxybenzoate 0.2
Disodium EDTA 0.05
Citric acid monohydrate 0.05
Isopropyl palmitate 4.0
Cetyl alcohol 3.5
Stearyl alcohol 2.5
Oleyl alcohol 2.0
Ceteareth-20 3.0
Sorbitan monostearate 2.0
Dimethicone 200 20 cs 0.5
Propyl para-hydroxybenzoate 0.1
Propylene glycol 2.0
Phenoxyethanol 1.0
10% sodium hydroxide qs pH
water qs 100,
as % by weight relative to the total weight of the composition.

8. The method according to claim 1, wherein the composition comprises:
Ivermectin 0.3
Glycerol 4.0
Acrylate C10-30 alkyl acrylate crosspolymer 0.2
Methyl para-hydroxybenzoate 0.2
Disodium EDTA 0.05
Citric acid monohydrate 0.05
Isopropyl palmitate 4.0
Cetyl alcohol 3.5
Stearyl alcohol 2.5
Oleyl alcohol 2.0
Ceteareth-20 3.0
Sorbitan monostearate 2.0
Dimethicone 200 20 cs 0.5
Propyl para-hydroxybenzoate 0.1
Propylene glycol 2.0
Phenoxyethanol 1.0
10% sodium hydroxide qs pH
water qs 100,
as % by weight relative to the total weight of the composition.

9. The composition of claim 1, wherein the concentration of ivermectin is 0.3% or 1.0% by weight, relative to the total weight of the composition.

* * * * *